(12) United States Patent
Luckemeyer et al.

(10) Patent No.: US 11,123,537 B2
(45) Date of Patent: Sep. 21, 2021

(54) APPARATUS FOR IRRIGATION WITH NEGATIVE PRESSURE

(71) Applicant: KCI Licensing, Inc., San Antonio, TX (US)

(72) Inventors: James A. Luckemeyer, San Antonio, TX (US); Timothy Mark Robinson, Shillingstone (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 572 days.

(21) Appl. No.: 15/580,563

(22) PCT Filed: Jun. 27, 2016

(86) PCT No.: PCT/US2016/039605
§ 371 (c)(1),
(2) Date: Dec. 7, 2017

(87) PCT Pub. No.: WO2017/003937
PCT Pub. Date: Jan. 5, 2017

(65) Prior Publication Data
US 2018/0185629 A1    Jul. 5, 2018

Related U.S. Application Data

(60) Provisional application No. 62/186,116, filed on Jun. 29, 2015.

(51) Int. Cl.
*A61M 39/28*    (2006.01)
*A61M 39/22*    (2006.01)
(Continued)

(52) U.S. Cl.
CPC ....... *A61M 39/284* (2013.01); *A61F 13/0206* (2013.01); *A61M 1/0058* (2013.01);
(Continued)

(58) Field of Classification Search
CPC ............ A61M 39/08; A61M 2039/082; A61M 39/28; A61M 1/0058; A61M 39/227; A61M 39/228
See application file for complete search history.

(56) References Cited

U.S. PATENT DOCUMENTS 1,355,846  A    10/1920  Rannells
2,547,758  A     4/1951  Keeling
(Continued)

FOREIGN PATENT DOCUMENTS

AU    550575 B2    3/1986
AU    745271 B2    3/2002
(Continued)

OTHER PUBLICATIONS

Extended European Search Report for Corresponding Application No. 182066860, dated Apr. 25, 2019.
(Continued)

*Primary Examiner* — Catharine L Anderson
*Assistant Examiner* — Arjuna P Chatrathi

(57) ABSTRACT

A system is described herein that can irrigate a tissue site using negative-pressure. The system may include a tissue interface configured to be placed adjacent to the tissue site, and a sealing member configured to be placed over the tissue interface to form a sealed space. The system may also include a negative-pressure source configured to be fluidly coupled to the sealed space and a fluid source. The system may further include an irrigation valve. The irrigation valve can have a fluid inlet configured to be fluidly coupled to the fluid source. The irrigation valve can also have a fluid outlet configured to be fluidly coupled to the sealed space. The irrigation valve may also include a clamp configured to be actuated by the negative-pressure source to regulate fluid flow from the fluid source through the fluid outlet.

29 Claims, 5 Drawing Sheets

(51) Int. Cl.
  *F16K 31/122* (2006.01)
  *F16K 7/06* (2006.01)
  *A61M 1/00* (2006.01)
  *A61F 13/02* (2006.01)
  *F16K 7/07* (2006.01)
  *F16K 7/20* (2006.01)

(52) U.S. Cl.
  CPC ............ *A61M 1/743* (2021.05); *A61M 1/774* (2021.05); *A61M 1/85* (2021.05); *A61M 1/90* (2021.05); *A61M 39/227* (2013.01); *A61M 39/228* (2013.01); *F16K 7/063* (2013.01); *F16K 7/07* (2013.01); *F16K 7/20* (2013.01); *F16K 31/1221* (2013.01); *A61M 2039/226* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,077,263 A * | 3/1978 | Brailsford ................ G01N 1/14 73/864.35 |
| 4,080,970 A | 3/1978 | Miller |
| 4,096,853 A | 6/1978 | Weigand |
| 4,131,399 A * | 12/1978 | Calvet ................ F04B 43/0072 417/477.12 |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,057,411 B2 | 11/2011 | Warlick et al. |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2009/0054855 A1* | 2/2009 | Blott ................ A61M 1/0088 604/290 |
| 2014/0163491 A1 | 6/2014 | Schuessler et al. |
| 2014/0224335 A1* | 8/2014 | Hofmann ................ B01L 3/502 137/1 |
| 2015/0080788 A1 | 3/2015 | Blott et al. |

(56) References Cited

U.S. PATENT DOCUMENTS

FOREIGN PATENT DOCUMENTS

| AU | 755496 B2 | 12/2002 |
|---|---|---|
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2515964 A2 | 10/2012 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax,"Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract,

(56) References Cited

OTHER PUBLICATIONS editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

\* cited by examiner

APPARATUS FOR IRRIGATION WITH NEGATIVE PRESSURE

RELATED APPLICATIONS

This present invention is the National Stage of International Application No. PCT/US2016/039605, entitled "Apparatus For Irrigation With Negative Pressure", filed Jun. 27, 2016 and claims the benefit of U.S. Provisional Patent Application No. 62/186,116, entitled "Apparatus for Irrigation with Negative Pressure," filed Jun. 29, 2015, all of which are incorporated herein by reference for all purposes.

TECHNICAL FIELD

The invention set forth in the appended claims relates generally to tissue treatment systems and more particularly, but without limitation, to an apparatus for application of a therapeutic fluid to tissue using negative pressure.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," and "vacuum-assisted closure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively.

While the clinical benefits of negative-pressure therapy and irrigation are widely known, the cost and complexity of negative-pressure therapy and irrigation therapy can be a limiting factor in its application, and the development and operation of negative-pressure systems, components, and processes and irrigation therapy systems, components, and processes could benefit manufacturers, healthcare providers, and patients.

BRIEF SUMMARY

New and useful systems, apparatuses, and methods for irrigating a tissue site in a negative-pressure therapy environment are set forth in the appended claims. Illustrative embodiments are also provided to enable a person skilled in the art to make and use the claimed subject matter. For example, a system is described herein that can irrigate a tissue site using negative-pressure. The system may include a tissue interface configured to be placed adjacent to the tissue site, and a sealing member configured to be placed over the tissue interface to form a sealed space. The system may also include a negative-pressure source configured to be fluidly coupled to the sealed space and a fluid source. The system may further include an irrigation valve. The irrigation valve can have a fluid inlet configured to be fluidly coupled to the fluid source. The irrigation valve can also have a fluid outlet configured to be fluidly coupled to the sealed space. The irrigation valve may also include a clamp configured to be actuated by the negative-pressure source to regulate fluid flow from the fluid source through the fluid outlet.

Alternatively, other example embodiments describe an irrigation valve. The irrigation valve can include a jaw configured to receive a tube, and a piston coupled to the jaw and operable to move the jaw in response to negative pressure. The piston may be operable to cycle the jaw between a high-flow position and a low-flow position to control fluid flow through the tube.

In another example embodiment, another irrigation valve is described. The irrigation valve can include a fluid bag configured to be fluidly coupled between a fluid source and a sealed space and a foam block encased in the fluid bag. The irrigation valve may have a fluid orifice configured to couple the fluid bag to the sealed space. The irrigation valve may also have a negative-pressure bag encasing the fluid bag and configured to be fluidly coupled to a negative-pressure source.

A method for irrigating a tissue site is also described herein, wherein some example embodiments include placing a tissue interface adjacent to the tissue site. The tissue interface and the tissue site can be covered to form a sealed space. An irrigation valve can be fluidly coupled to the sealed space, and a fluid source can be fluidly coupled to the irrigation valve. A negative-pressure source can be fluidly coupled to the sealed space and the irrigation valve and operated to supply negative-pressure to the sealed space and the irrigation valve. A fluid path through the irrigation valve can be restricted in response to the supply of negative pressure.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientations assume a frame of reference consistent with or relative to a patient in a position to receive treatment. However, as should be recognized by those skilled in the art, this frame of reference is merely a descriptive expedient rather than a strict prescription.

Figure 1:
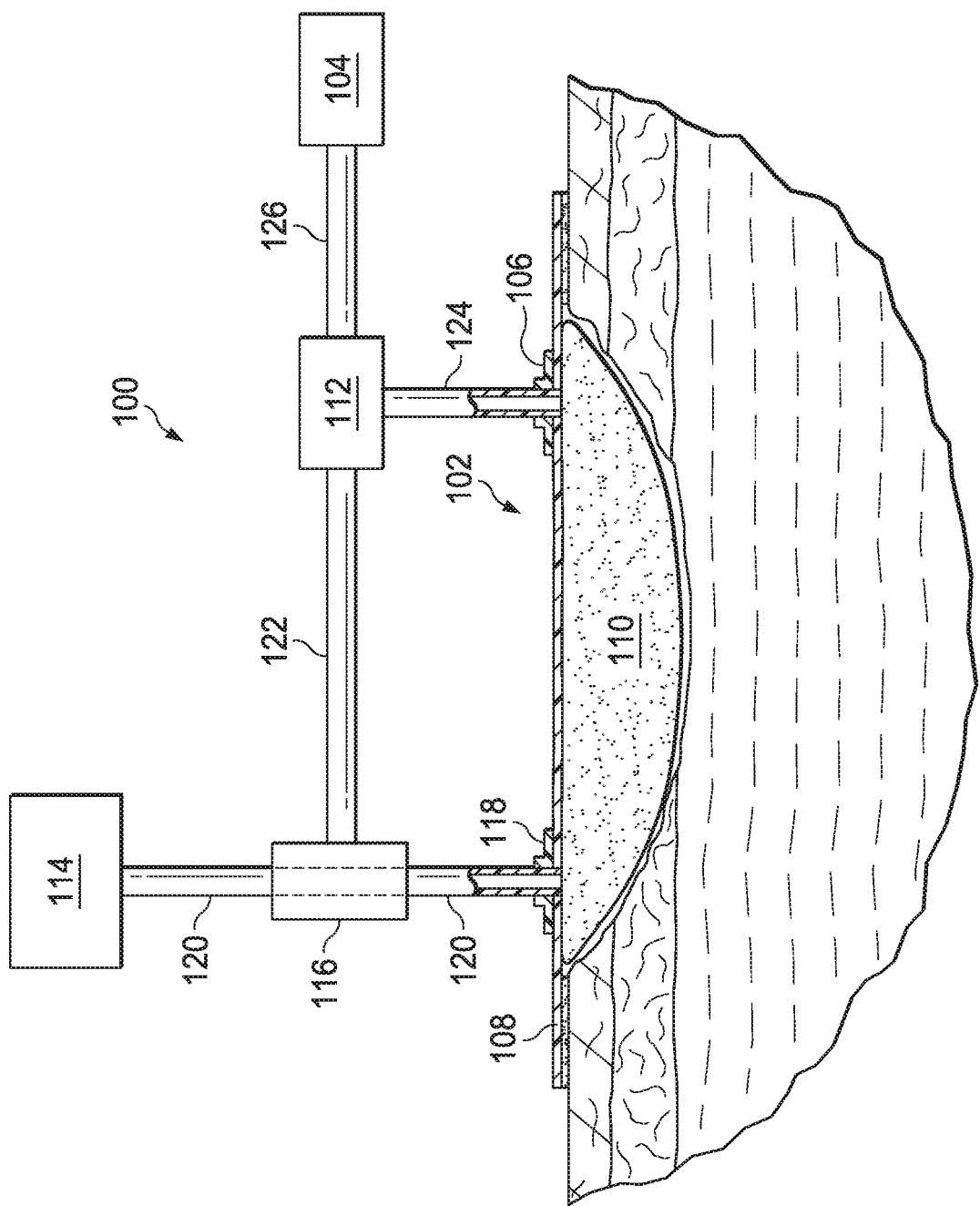
FIG. 1 is a schematic diagram of an example embodiment of a negative-pressure therapy system that can irrigate a tissue site in accordance with this specification.

FIG. 1 is a schematic diagram of an example embodiment of a therapy system 100 that can irrigate a tissue site in accordance with this specification. The therapy system 100 may include a dressing and a negative-pressure source. For example, a dressing 102 may be fluidly coupled to a negative-pressure source 104, as illustrated in FIG. 1. In some embodiments, the negative-pressure source 104 may be fluidly coupled to the dressing 102 through a fluid interface, such as a connector 106. A dressing generally includes a cover and a tissue interface. The dressing 102, for example, may include a cover 108, and a tissue interface 110. The therapy system 100 may also include a fluid container, such as a container 112, coupled to the dressing 102 and to the negative-pressure source 104.

In some embodiments, the therapy system 100 may provide irrigation of the tissue site. The therapy system 100 may include a fluid source and an irrigation valve. For example, the therapy system 100 may include a fluid source 114 fluidly coupled to an irrigation valve 116. The irrigation valve 116 may be fluidly coupled to the dressing 102 through a fluid interface, such as a connector 118.

In general, components of the therapy system 100 may be coupled directly or indirectly. For example, the negative-pressure source 104 may be directly coupled to the container 112 and indirectly coupled to the dressing 102 through the container 112. Components may be fluidly coupled to each other to provide a path for transferring fluids (i.e., liquid and/or gas) between the components.

In some embodiments, components may be fluidly coupled through a tube. For example, the negative-pressure source may be fluidly coupled to the container 112 through a tube 126. The dressing 102 may be fluidly coupled to the container 112 by a tube 124, and the container 112 may be fluidly coupled to the irrigation valve 116 by a tube 122. In some embodiments, the irrigation valve 116 may be fluidly coupled to the dressing 102 by a tube 120. A "tube," as used herein, broadly refers to a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

In operation, the tissue interface 110 may be placed within, over, on, or otherwise proximate to a tissue site. The cover 108 may be placed over the tissue interface 110 and sealed to tissue near the tissue site. For example, the cover 108 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site through the tissue interface 110 in the sealed therapeutic environment can induce macrostrain and microstrain in the tissue site, as well as remove exudates and other fluids from the tissue site, which can be collected in container 112 and disposed of properly.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies a position in a fluid path relatively closer to a negative-pressure source, and conversely, the term "upstream" implies a position relatively further away from a negative-pressure source. Similarly, it may be convenient to describe certain features in terms of fluid "inlet" or "outlet" in such a frame of reference. This orientation is generally presumed for purposes of describing various features and components of therapy systems herein. However, the fluid path may also be reversed in some applications (such as by substituting a positive-pressure source for a negative-pressure source or a negative-pressure source for a fluid source) and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be used in certain tissue areas to grow additional tissue that may be harvested and transplanted to another tissue location.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure.

A negative-pressure source, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure source may be housed within or used in conjunction with other components, such as sensors, processing units, alarm indicators, memory, databases, software, display devices, or user interfaces that further facilitate negative-pressure therapy. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

The tissue interface 110 can be generally adapted to contact a tissue site. The tissue interface 110 may be partially or fully in contact with the tissue site. If the tissue site is a wound, for example, the tissue interface 110 may partially or completely fill the wound, or may be placed over the wound. The tissue interface 110 may take many forms, and may have many sizes, shapes, or thicknesses depending on a variety of factors, such as the type of treatment being implemented or the nature and size of a tissue site. For example, the size and shape of the tissue interface 110 may be adapted to the contours of deep and irregular shaped tissue sites.

In some embodiments, the tissue interface 110 may be a manifold. A "manifold" in this context generally includes any substance or structure providing a plurality of pathways adapted to collect or distribute fluid across a tissue site under negative pressure. For example, a manifold may be adapted to receive negative pressure from a source and distribute the negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be channels interconnected to improve distribution or collection of fluids across a tissue site. For example, cellular foam, open-cell foam, reticulated foam, porous tissue collections, and other porous material such as gauze or felted mat generally include pores, edges, and/or walls adapted to form interconnected fluid pathways. Liquids, gels, and other foams may also include or be cured to include apertures and flow channels. In some illustrative embodiments, a manifold may be a porous foam material having interconnected cells or pores adapted to uniformly (or quasi-uniformly) distribute negative pressure to a tissue site. The foam material may be either hydrophobic or hydrophilic. In one non-limiting example, a manifold may be an open-cell, reticulated polyurethane foam such as GranuFoam® dressing available from Kinetic Concepts, Inc. of San Antonio, Tex.

In an example in which the tissue interface 110 may be made from a hydrophilic material, the tissue interface 110 may also wick fluid away from a tissue site, while continuing to distribute negative pressure to the tissue site. The wicking properties of the tissue interface 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 110 may further promote granulation at a tissue site when pressure within the sealed therapeutic environment is reduced. For example, any or all of the surfaces of the tissue interface 110 may have an uneven, coarse, or jagged profile that can induce microstrains and stresses at a tissue site if negative pressure is applied through the tissue interface 110.

In some embodiments, the tissue interface 110 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 110 may further serve as a scaffold for new cell-growth, or a scaffold material may be used in conjunction with the tissue interface 110 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, a sealing member, such as the cover 108 may provide a bacterial barrier and protection from physical trauma. The cover 108 may also be constructed from a material that can reduce evaporative losses and provide a fluid seal between two components or two environments, such as between a therapeutic environment and a local external environment. The cover 108 may be, for example, an elastomeric film or membrane that can provide a seal adequate to maintain a negative pressure at a tissue site for a given negative-pressure source. In some example embodiments, the cover 108 may be a polymer drape, such as a polyurethane film, that is permeable to water vapor but impermeable to liquid. Such drapes typically have a thickness in the range of about 25 microns to about 50 microns. For permeable materials, the permeability generally should be low enough that a desired negative pressure may be maintained.

An attachment device may be used to attach the cover 108 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 108 may be coated with an acrylic adhesive having a coating weight between about 25 grams per square meter to about 65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

In some embodiments, the dressing 102 may also include a fluid interface, such as the connector 106, configured to fluidly couple the negative-pressure source 104 to the sealed therapeutic environment formed by the cover 108. In some embodiments, the fluid interface may include a flange portion that couples to the cover 108 and a portion that fluidly couples to a tube. In one exemplary embodiment, the fluid interface may be a T.R.A.C.® Pad or Sensa T.R.A.C.® Pad available from Kinetic Concepts, Inc. of San Antonio, Tex. In other exemplary embodiments, a tube may be inserted through the cover 108. Such a fluid interface can allow negative pressure to be delivered to the sealed therapeutic environment. For example, a fluid interface can provide a fluid conductor through the cover 108 to the tissue interface 110. In some embodiments, a fluid interface can also provide more than one fluid path through the cover 108 or merge more than one fluid conductor into a single fluid path.

The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

The fluid source 114 is representative of a container, canister, pouch, or other fluid storage component, which can be used to manage an irrigation fluid to be provided to the tissue site. In some embodiments, the fluid source 114 may be an intravenous (IV) fluid bag suspended from an intravenous pole. In other embodiments, the fluid source 114 may be another fluid storage device positioned proximate to a tissue site. In some embodiments, the fluid source 114 may be positioned vertically above the tissue site. In other embodiments, the fluid source 114 may be positioned vertically level or below the tissue site.

In some embodiments, the dressing 102 may also include a fluid interface, such as the connector 118, configured to fluidly couple the irrigation valve 116 to the sealed therapeutic environment formed by the cover 108. In some embodiments, the fluid interface may include a flange portion that couples to the cover 108 and a portion that fluidly couples to a tube. In other exemplary embodiments, a tube may be inserted through the cover 108. Such a fluid interface can allow fluid to be delivered to the sealed therapeutic environment. For example, a fluid interface can provide a fluid conductor through the cover 108 to the tissue interface 110. In some embodiments, a fluid interface can also provide more than one fluid path through the cover 108 or merge more than one fluid conductor into a single fluid path.

Irrigation therapy may provide a continuous or near continuous supply of fluids to a tissue site. The fluids may flow across a tissue site and remove undesired products of the healing process. For example, irrigation therapy may help remove necrotic tissue, bacteria, exudates, dirt, or other substances from the tissue site. Generally, saline may be used as an irrigation fluid. Saline can provide good infection control, and if needed, additional fluids may be added to the saline or may be provided in combination with saline to address specific issues of a particular tissue site.

Unlike instillation therapy, irrigation therapy does not include a dwell time; instead, fluids are continually moved across the tissue site. The continuous movement of fluid can use a large amount of fluid and can require frequent changing of waste fluid containers. Irrigation therapy may also require use of dedicated equipment. Often, the systems for providing irrigation therapy may not interact well with other therapy systems. For example, an irrigation therapy system often requires a pump to move irrigation fluid to and across a tissue site. If the irrigation therapy system is paired with a negative-pressure therapy system coordination of multiple pumps may be necessary to prevent over or under pressurization of the tissue site or other negative interactions between the pumps. Often a clinician may be required to closely monitor the operation of both systems to ensure that both therapies are properly provided. The need for dedicated irrigation therapy equipment can also prove problematic in mobile situations, such as in emergency medical vehicles or small trauma centers. There, space may be at a premium and many users may choose to only provide one type of therapy device. Consequently, many patients do not receive beneficial irrigation therapy.

In some embodiments, the therapy system 100 can provide negative-pressure therapy to the tissue site. In some embodiments, the therapy system 100 can also provide irrigation therapy. For example, the therapy system 100 can be fluidly coupled to the irrigation valve 116. Operation of the therapy system 100 can actuate the irrigation valve 116 to draw fluid through the irrigation valve 116 to the tissue site. By using the therapy system 100 to actuate irrigation therapy, the rate at which fluids can be provided to a tissue site may be controlled by the application of negative-pressure. Furthermore, the irrigation valve 116 can provide irrigation therapy without requiring additional devices, such as a dedicated irrigation pump.

Figure 2A:
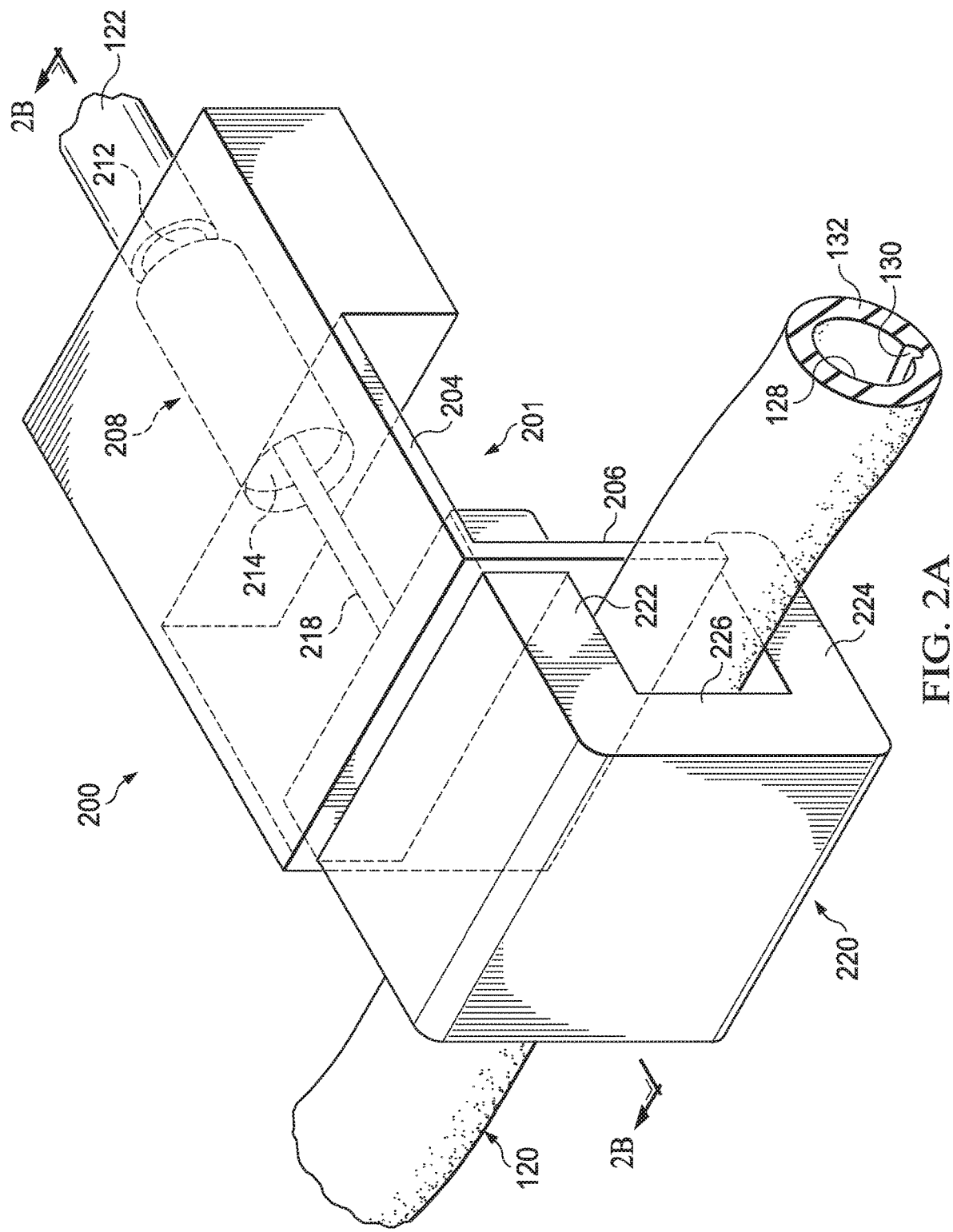
FIG. 2A is a perspective view illustrating additional details that may be associated with an example embodiment of an irrigation valve of the negative-pressure therapy system of FIG. 1.

FIG. 2A is a perspective view illustrating additional details that may be associated an irrigation valve 200 that can be used with some embodiments of the therapy system 100 of FIG. 1. The irrigation valve 200 may include a clamp 201 operatively coupled to the tube 120.

Figure 2B:
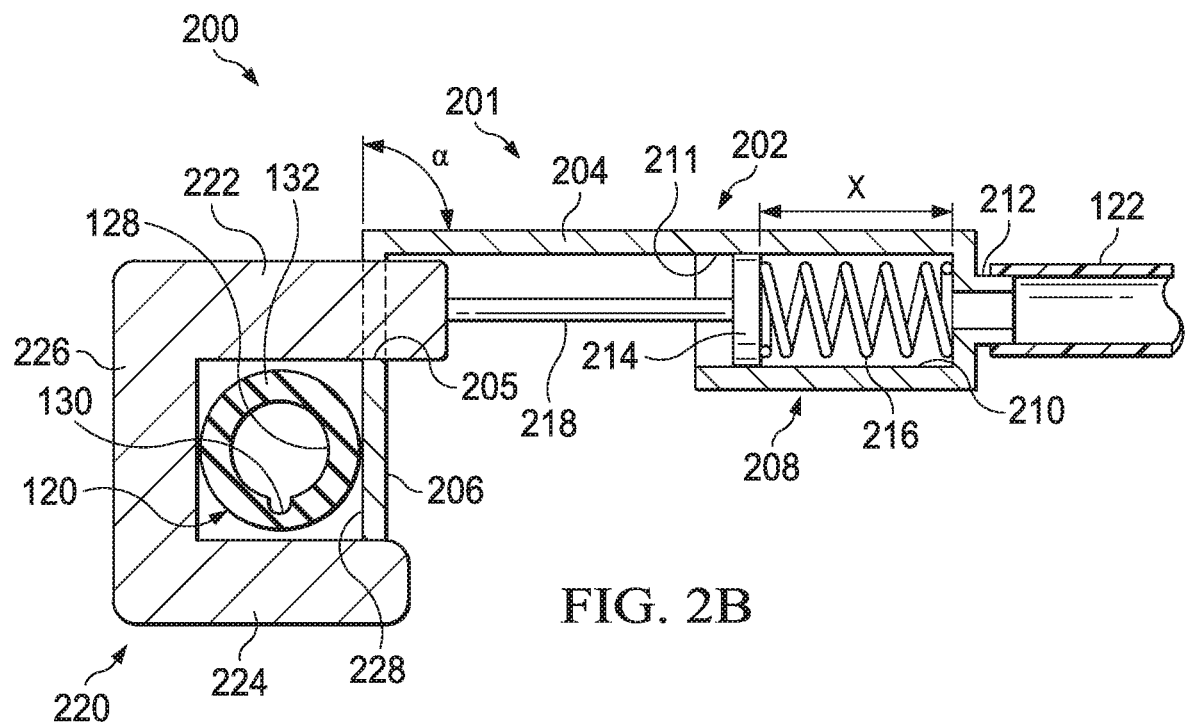
FIG. 2B is a schematic sectional view illustrating additional details that may be associated with the irrigation valve of FIG. 2A in a high-flow position.

FIG. 2B is a schematic sectional view illustrating additional details that may be associated with some example embodiments of an irrigation valve 200 in a first position or a high-flow position that may be used with some embodiments of the therapy system 100. The irrigation valve 200 may be an example embodiment of the irrigation valve 116 of FIG. 1.

The clamp 201 may include a base 202 having a first plate, such as a first bar 204, and a second plate, such as a second bar 206. The first bar 204 may be a generally flat member having a length, width, and thickness. In some embodiments, the length of the first bar 204 may be greater than a width of the first bar 204 so that the first bar 204 may be rectangular in shape having a first end and a second end. The thickness of the first bar 204 may be less than the width of the first bar 204. In other embodiments, the first bar 204 may have other shapes, for example, square, circular, triangular, or an amorphous shape. The first bar 204 may be formed of a material that is relatively rigid, such as metals, ceramics, or hard plastics. In some embodiments, the first bar 204 may be resistant to deformation in compression and buckling if a compressive load is applied at the first and second ends of the first bar 204. For example, if a pressure of about 120 mm Hg is used to generate a compressive loading at the first and second ends of the first bar 204, the first bar 204 may deflect, but the first bar 204 may not suffer a catastrophic failure.

Similarly, the second bar 206 may be a generally flat member having a length, width, and thickness. In some embodiments, the length of the second bar 206 may be greater than a width of the second bar 206 so that the second bar 206 may be rectangular in shape having a first end and a second end. The thickness of the second bar 206 may be less than the width of the second bar 206. The second bar 206 may be formed of a material that is relatively rigid, for example metals, ceramics, or hard plastics. The second bar 206 may be resistant to buckling if a load is applied proximate to a center of the second bar 206.

The first bar 204 and the second bar 206 may be coupled at ends of the first bar 204 and the second bar 206. For example, the second end of the first bar 204 may be coupled to the first end of the second bar 206. In some embodiments, the first bar 204 and the second bar 206 may form an L-shape if coupled together. In other embodiments, the first bar 204 and the second bar 206 may form a T-shape. The first bar 204 and the second bar 206 may form an angle α if coupled. In some embodiments, the angle α may be about 90 degrees. In other embodiments, the angle α may be between about 15 degrees and about 165 degrees. The first bar 204 and the second bar 206 may be bonded, welded, adhered, or otherwise joined. In other embodiments, the first bar 204 and the second bar 206 may be formed of a single piece of material that is formed to have the angle α.

In some embodiments, the second bar 206 may have an opening or an aperture 205. The aperture 205 may be positioned proximate to the location where the second bar 206 is coupled to the first bar 204. The aperture 205 may extend completely through the second bar 206.

The clamp 201 may also include a piston 208. The piston 208 may be coupled to the first end of the first bar 204. In some embodiments, the piston 208 may be located on a side of the first bar 204. For example, the piston 208 may be located on a same side of the first bar 204 as the second bar 206. The piston 208 may include a chamber 210 having a fluid outlet 212. The chamber 210 may be a pressure vessel configured to maintain pressures substantially different than an ambient pressure. The chamber 210 may have a length that is generally parallel to the length of the first bar 204. The fluid outlet 212 may be a fluid port fluidly coupled to the chamber 210. In some embodiments, the fluid outlet 212 may be located on an end of the chamber 210 proximate to the first end of the first bar 204. In other embodiments, the fluid outlet 212 may be located elsewhere on the chamber 210. The fluid outlet 212 may provide a fluid communication path between the ambient environment and the chamber 210. In some embodiments, the fluid outlet 212 may be configured to be fluidly coupled to another device, such as the tube 122. The chamber 210 may have an open end 211 opposite the fluid outlet 212.

A piston head 214 and a biasing member 216 may be disposed in the chamber 210. The piston head 214 may be a solid object configured to fluidly isolate the chamber 210 from the open end 211. In other embodiments, the piston head 214 may have a fluid path across the piston head 214 from the chamber 210 to the ambient environment. For example, the piston head 214 may have a valved passage operable to permit fluid communication across the piston head 214 if a pressure in the chamber 210 is about or exceeds a threshold pressure. The piston head 214 may be disposed in the chamber 210 between the open end 211 and the fluid outlet 212. In some embodiments, if the chamber 210 is cylindrically-shaped, the piston head 214 may be a disc having perimeter dimensions so that the piston head 214 may form a fluid seal with interior surfaces of the chamber 210. In some embodiments, an o-ring or other sealing member may fluidly seal the piston head 214 to the chamber 210. The piston head 214 may be moveable within the chamber 210. In some embodiments, the piston head 214 can move parallel to a length of the chamber 210 and the first bar 204 while maintaining the fluid seal. The piston head 214 may have a first position proximate to the open end 211 and a second position proximate to the fluid outlet 212.

The fluid seal between the piston head 214 and the interior surfaces of the chamber 210 may permit a differential force to be developed across the piston head 214. For example, if fluid is drawn from the chamber 210 through the fluid outlet 212, a pressure less than an ambient pressure surrounding the piston 208 may be developed in the chamber 210. The differential pressure between the ambient pressure and the pressure in the chamber 210 across the piston head 214 may generate a differential force that urges the piston head 214 to move toward the fluid outlet 212. Similarly, if a fluid is forced into the chamber 210 through the fluid outlet 212, a pressure greater than the ambient pressure surrounding the piston 208 may be developed in the chamber 210. The differential pressure across the piston head 214 may generate a differential force that urges the piston head 214 to move away from the fluid outlet 212.

Generally, the differential force that can be exerted on the piston head 214 is proportional to the difference in pressures in the chamber 210 and the ambient environment and the surface area of the piston head 214 exposed to the chamber 210. For example, the size of the piston head 214 may be increased to increase the potential differential force that can be exerted. Similarly, the difference between the pressure in the ambient environment and the pressure in the chamber 210 can be increased to increase the exerted differential force.

The biasing member 216 may be disposed in the chamber between the piston head 214 and the fluid outlet 212. The biasing member 216 may have a first end proximate to the fluid outlet 212 and a second end proximate to the piston head 214. In some embodiments, the biasing member 216 may be a spring. As shown in FIG. 2B, the biasing member 216 may be in a relaxed position. Generally, a spring, such as the biasing member 216, may exert a force that is proportional to a distance the spring is moved from a relaxed position. In some embodiments, the biasing member 216 may have a length X if the biasing member 216 is in the relaxed position. The biasing member 216 may bias the piston head 214 away from the fluid outlet 212 to the first position proximate to the open end 211.

The clamp 201 may also include a rod 218. The rod 218 may be coupled to the piston head 214 on a side that is opposite the biasing member 216. The rod 218 may be a cylindrical member extending toward the second bar 206. In other embodiments, the rod 218 may not be cylindrical. The rod 218 may have a perimeter dimension, such as a diameter, that is less than the perimeter dimension of the piston head 214 and a length that is less than a length of the first bar 204. Generally, the rod 218 may be parallel to the first bar 204.

The clamp 201 may also include a jaw 220 having a first leg 222, a second leg 224, and a cross leg 226. The first leg 222 may have a first end coupled to the rod 218 on an opposite end of the rod 218 from the piston head 214. The first leg 222 may extend through the aperture 205 of the second bar 206. The first leg 222 may be a rectangular body having a length, width, and thickness. Generally, the length of the first leg 222 may be greater than a width or outer diameter of the tube 120. In some embodiments, the first leg 222 may be a portion of the rod 218 that extends through the aperture 205 beyond the second bar 206.

The cross leg 226 may be coupled to an end of the first leg 222 opposite of the rod 218. The cross leg 226 may be parallel to the second bar 206 and have a length, width, and thickness. Generally, the length of the cross leg 226 may be greater than a width or outer diameter of the tube 120. In some embodiments, the cross leg 226 may have a length such that, the end of the cross leg 226 extends beyond an end of the second bar 206. In other embodiments, the cross leg 226 may have an end opposite the first leg 222 that is coextensive with the second end of the second bar 206.

The second leg 224 may be coupled to an end of the cross leg 226 that is opposite the first leg 222. The second leg 224 may extend from the cross leg 226 toward the second bar 206. In some embodiments, the second leg 224 may be parallel to the first leg 222 and have a length such that an end of the second leg 224 that is opposite the cross leg 226 may extend beyond the end of the second bar 206. The first leg 222, the second leg 224, the cross leg 226, and the second bar 206 may form a passageway 228, through which a tube, such as the tube 120 may be inserted. In other embodiments, the jaw 220 may be formed with the first leg 222 and the cross leg 226.

The tube 120 may be a tube having a tube wall 132 and a lumen 128. In some embodiments, the tube 120 may also include a recess 130. A tube is an elongated, cylindrical structure with some flexibility, but the geometry and rigidity may vary. The tube wall 132 may be formed from a polyurethane, silicone, or other material, for example. The lumen 128 may be a passage extending a length of the tube 120 and may be suitable for passage of fluid. In some embodiments, if a pressure differential of about 75 mm Hg exists across ends of the lumen 128, the lumen 128 may accommodate a flow rate of about 10 cubic centimeters a minute. A pressure differential across the lumen 128 may refer to a difference in pressures between the pressure at a first end of the lumen 128 and the pressure at a second end of the lumen 128. The first end of the lumen 128 may be coupled to a fluid source, such as the fluid source 114. In some embodiments, the first end of the lumen 128 may be referred to as a fluid inlet of the irrigation valve 200. The second end of the lumen 128 may be coupled to the sealed therapeutic environment, such as through the connector 118. In some embodiments, the second end of the lumen 128 may be referred to as a fluid outlet of the irrigation valve 200. The recess 130 may be a notch or other recess formed in the lumen 128. In some embodiments, the recess 130 may extend the length of the tube 120. In other embodiments, the recess 130 may have a length similar to a length of the second bar 206. In some embodiments, if a pressure differential of about 125 mm Hg exists across ends of the recess 130, the recess 130 may accommodate a flow rate of about 0.5 cubic centimeters a minute.

The fluid outlet 212 may be fluidly coupled to a negative-pressure source, such as the negative-pressure source 104. For example, the tube 122 may be coupled to the fluid outlet 212 and the negative-pressure source 104. In some embodiments, the tube 122 may also be fluidly coupled to the connector 106. Similarly, the tube 120 may be fluidly coupled to the fluid source 114 and the connector 118. The tube 120 may be passed through the passageway 228. If the recess 130 is less than a length of the tube 120, the recess 130 may be positioned proximate to the second bar 206.

The negative-pressure source 104 may be operated to draw fluid from the sealed therapeutic environment and the chamber 210, generating a negative pressure in the sealed space and the chamber 210. In some embodiments, the negative-pressure source 104 may maintain a negative pressure of about 75 mm Hg in the sealed space and the chamber 210.

Generally, the biasing member 216 may exert a reactive force proportional to the distance the biasing member 216 is compressed. For example, if the second end of the biasing member 216 is moved toward the first end of the biasing member 216, compressing the biasing member 216 from the length X to the length $X_1$, the biasing member 216 may exert a reactive force that is proportional to the distance $X-X_1$, i.e., the amount the biasing member 216 is compressed. In some embodiments, the biasing member 216 may be selected to compress in response to a particular negative pressure, or threshold pressure. In some embodiments, the threshold pressure may be about 75 mm Hg of negative pressure. In other embodiments, the threshold pressure may be greater than or less than about 75 mm Hg negative pressure.

If the differential force exerted by the differential pressure developed by the removal of fluid by the negative-pressure source 104 in the chamber 210 is insufficient to overcome the reactive force of the biasing member 216, the piston head 214 may remain at the first position illustrated in FIG. 2B. In response, the rod 218 and the jaw 220 may not move, remaining in a first or an open position. In the open position, fluid may flow through the tube 120 from the fluid source 114 to the sealed therapeutic environment. Generally, the rate of fluid flow may be limited only by the flow rate that can be accommodated by the lumen 128 at a pressure differential across the lumen 128. In some embodiments, if the pressure differential between the sealed space and the ambient environment is about 75 mm Hg, the flow rate may be about 10 cubic centimeters a minute through the lumen 128.

Fluid may flow through the tube 120 to the sealed therapeutic environment in response to the force of gravity, i.e., gravity fed. Fluid flow through the tube 120 may also be aided by the difference in pressure between the pressure in the sealed therapeutic environment and the ambient environment. Fluid in the fluid source 114, fluidly coupled to the sealed therapeutic environment by the tube 120, may be at the same pressure as the pressure in the sealed therapeutic environment. If the pressure in the sealed therapeutic environment is less than the ambient pressure, such as if the negative-pressure source 104 is operating to draw fluid from the sealed therapeutic environment, fluid may move to the sealed therapeutic environment through the irrigation valve 200.

Figure 2C:
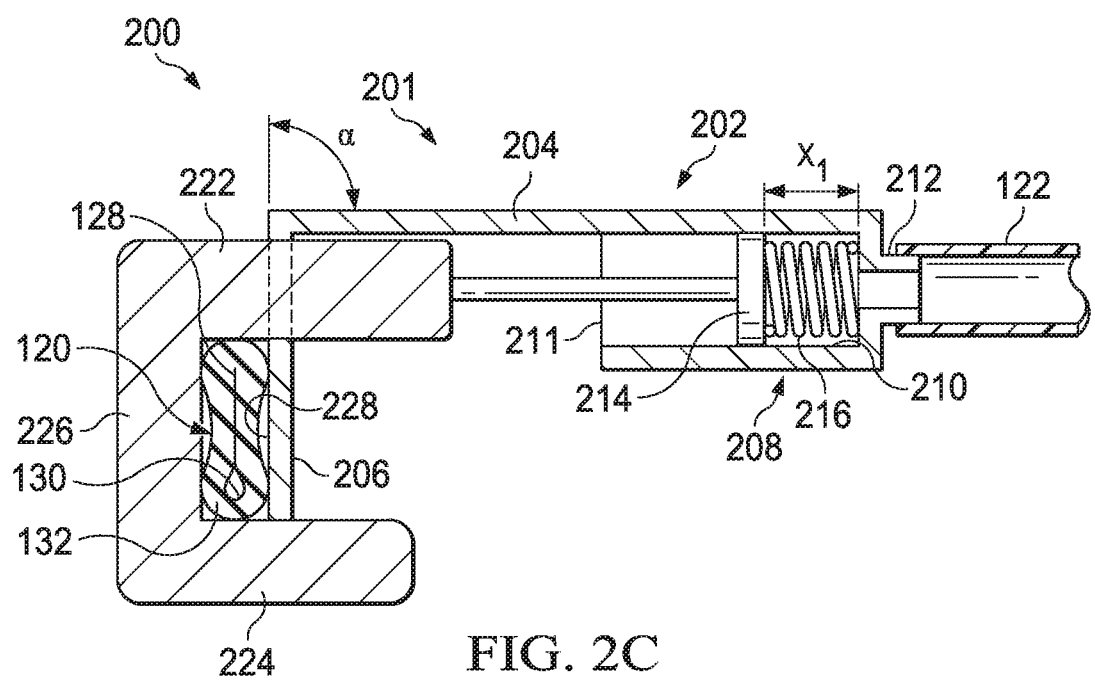
FIG. 2C is a schematic sectional view illustrating additional details of the irrigation valve of FIG. 2A in a low-flow position.

FIG. 2C is a schematic sectional view illustrating additional details of the irrigation valve 200 in a second or low-flow position. If the negative-pressure source 104 continues to operate, the negative pressure in the sealed therapeutic environment and in the chamber 210 may increase. In some embodiments, the negative-pressure source 104 may operate until the negative pressure in the sealed therapeutic environment and in the chamber 210 is about 125 mm Hg. In response, the pressure differential across the piston head 214 may overcome the reactive force of the biasing member 216, causing the piston head 214 to move toward the fluid outlet 212 and compressing the biasing member 216 to the $X_1$ position. As the piston head 214 moves toward the fluid outlet 212, the rod 218 can move the jaw 220 toward the second bar 206 to the low-flow position. The cross leg 226 may compress the tube 120 against the second bar 206, as shown in FIG. 2C. The force applied to the tube 120 by the cross leg 226 and the second bar 206 may be proportional to the differential pressure across the piston head 214 and the surface area of the piston head 214. As the tube 120 is compressed between the jaw 220 and the second bar 206, the first leg 222 and the second leg 224 may maintain the position of the tube 120 between the cross leg 226 and the second bar 206, preventing slippage of the tube 120.

Compression of the tube 120 by the cross leg 226 may at least partially compress or block the lumen 128, preventing or limiting fluid communication through the lumen 128. The recess 130 may remain open. Generally, the rate of fluid flow may be limited only by the flow rate that can be accommodated by the recess 130 at the pressure differential across the recess 130. In some embodiments, if the pressure differential between the sealed space and the ambient environment is about 125 mm Hg, the flow rate may be maintained at about 0.5 cubic centimeters per minute through the recess 130.

If the negative-pressure source 104 is turned off, the negative pressure in the chamber 210 and in the sealed space adjacent to the tissue site may gradually decrease and equalize with the ambient pressure. In response, the reactive force of the biasing member 216 may urge the piston head 214 away from the fluid outlet 212. Similarly, the coupled rod 218 and the jaw 220 may move from the low-flow position of FIG. 2C to the high-flow position of FIG. 2B. Movement of the jaw 220 to the high-flow position can open the lumen 128 of the tube 120 and allow fluid to flow to the sealed space adjacent to the tissue site at a higher flow rate, for example, about 10 cubic centimeters per minute.

In some embodiments, the irrigation valve 200 may be actuated by the negative-pressure source 104 to provide irrigation therapy. The negative-pressure source 104 may be turned on and set to provide an intermittent therapy. The negative-pressure source 104 may remove fluid from the tissue site to develop and maintain the negative pressure at the tissue site at about 125 mm Hg. During this time, the negative pressure developed at the tissue site may be communicated to the chamber 210. In response, the piston head 214 be drawn toward the fluid outlet 212, compressing the biasing member 216 and the tube 120 with the jaw 220, restricting fluid flow to the recess 130. Fluid flow through the recess 130 may be about 0.5 cubic centimeters per minute. In some embodiments, the negative-pressure source 104 may maintain the negative pressure at about 125 mm Hg for about 60 minutes, providing about 30 cubic centimeters (cc) of fluid to the tissue site.

In some embodiments, the negative-pressure source 104 may stop developing negative-pressure for about 10 minutes. During this time period, the negative pressure at the tissue site and the fluidly coupled chamber 210 may decrease. In response, the biasing member 216, compressed to the length $X_1$, may exert a force on the piston head 214, moving the piston head 214 toward the open end 211 and uncompressing the tube 120 with the jaw 220. Fluid may flow into the tissue site at about 10 cc/minute, providing about 100 cc of fluid to the tissue site.

Figure 3A:
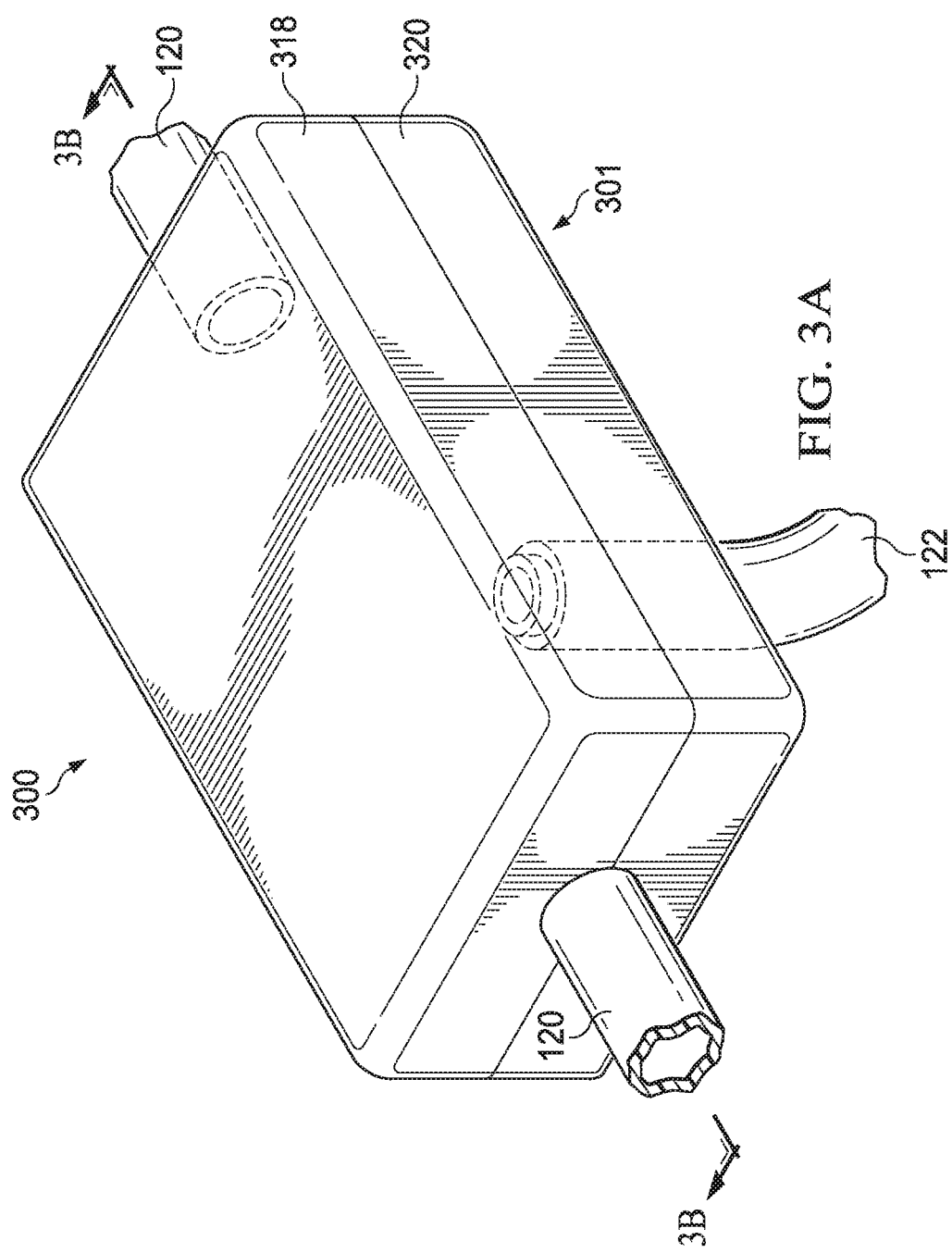
FIG. 3A is a perspective view illustrating additional details that may be associated with an example embodiment of another irrigation valve of the negative-pressure therapy system of FIG. 1.
Figure 3B:
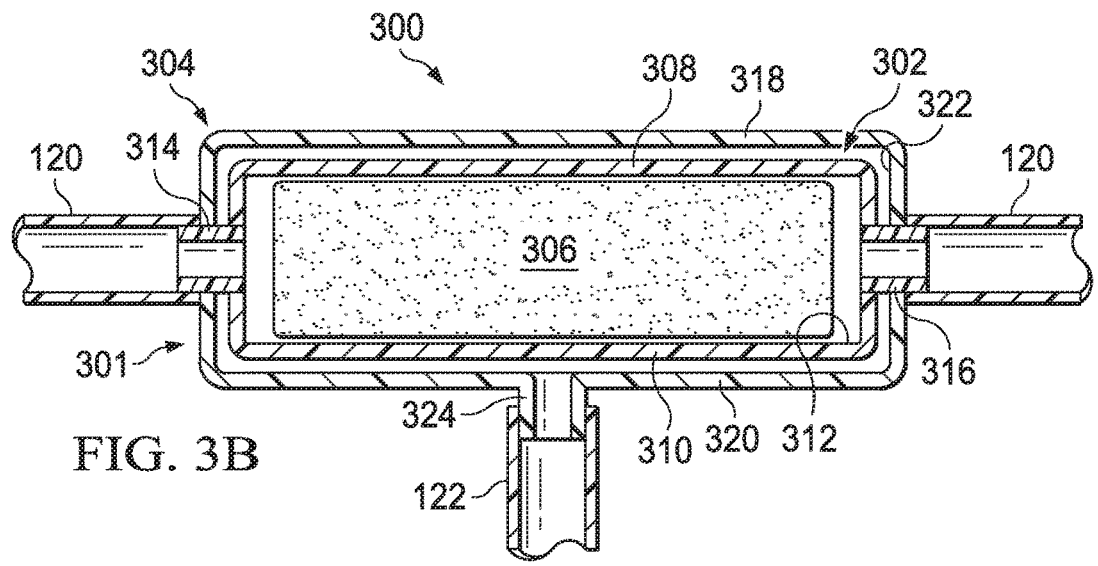
FIG. 3B is a schematic sectional view illustrating additional details of the irrigation valve of FIG. 3A in a high-flow position.
Figure 3C:
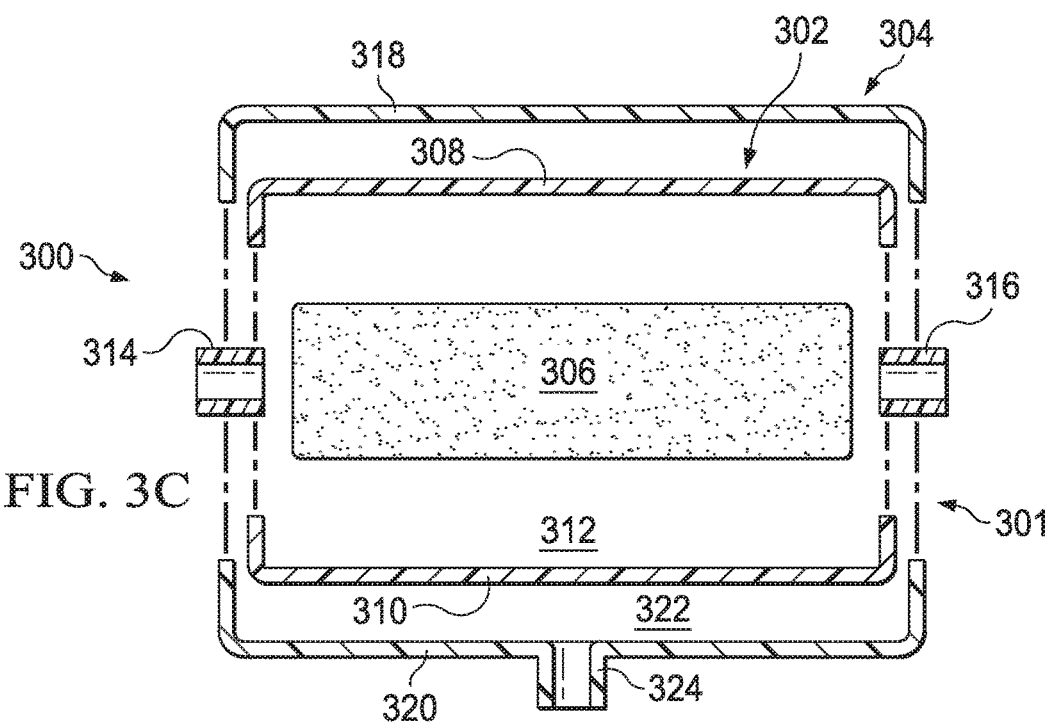
FIG. 3C is a schematic assembly view illustrating additional details of the irrigation valve of FIG. 3A.

FIG. 3A is a perspective view illustrating additional details that may be associated with an irrigation valve 300 that can be used with some embodiments of the therapy system 100 of FIG. 1. FIG. 3B is a schematic sectional view illustrating additional details that may be associated with some example embodiments of the irrigation valve 300 in a high-flow position that may be used with some embodiments of the therapy system 100. For example, the irrigation valve 300 may be an example of the irrigation valve 116 of FIG. 1. FIG. 3C is a sectional assembly view of the irrigation valve 300 illustrating additional details that may be associated with some embodiments. The irrigation valve 300 may include a fluid inlet 314, a fluid outlet 316, and a clamp 301. The clamp 301 can include a fluid bag, such as a fluid enclosure 302, and a negative-pressure bag, such as a pressure enclosure 304.

The fluid enclosure 302 may include a liquid spacer or spacer, such as a foam block 306. The foam block 306 may be a substance or structure providing a plurality of pathways adapted to distribute fluid through the fluid enclosure 302. The pathways of the foam block 306 may be channels interconnected to improve distribution of fluids across the fluid enclosure 302. For example, cellular foam, open-cell foam, reticulated foam, porous tissue collections, and other porous material such as gauze or felted mat generally include pores, edges, and/or walls adapted to form interconnected fluid pathways. Liquids, gels, and other foams may also include or be cured to include apertures and flow channels. In some illustrative embodiments, the foam block 306 may be a porous foam material having interconnected cells or pores adapted to uniformly (or quasi-uniformly) distribute fluid through the fluid enclosure 302. The foam material may be either hydrophobic or hydrophilic. In one non-limiting example, the foam block 306 may be an open-cell, reticulated polyurethane foam such as GranuFoam® dressing available from Kinetic Concepts, Inc. of San Antonio, Tex.

In some embodiments, the foam block 306 may act as a biasing member or a spring. For example, foam materials may have an elastic modulus, which may also be referred to as a foam modulus. Generally, the elastic modulus of a material may measure the resistance of the material to elastic deformation under a load. The elastic modulus of a material may be defined as the slope of a stress-strain curve in the elastic deformation region of the curve. The elastic deformation region of a stress-strain curve represents that portion of the curve where a deformation of a material due to an applied load is elastic, that is, not permanent. If the load is removed, the material may return to its pre-loaded state. Stiffer materials may have a higher elastic modulus, and more compliant materials may have a lower elastic modulus. Generally, reference to the elastic modulus of a material refers to a material under tension.

For some materials under compression, the elastic modulus can be compared between materials by comparing the compression force deflection (CFD) of the materials. Typically, CFD is determined experimentally by compressing a sample of a material until the sample is reduced to about 25% of its uncompressed size. The load applied to reach the 25% compression of the sample is then divided by the area of the sample over which the load is applied to arrive at the CFD. The CFD can also be measured by compressing a sample of a material to about 50% of the sample's uncompressed size. The CFD of a foam material can be a function of compression level, polymer stiffness, cell structure, foam density, and cell pore size.

Furthermore, CFD can represent the tendency of a foam to return to its uncompressed state if a load is applied to compress the foam. For example, a foam having a CFD of about 4 kPa may exert about 4 kPa in reaction to 25% compression. The CFD of the foam block 306 may represent the ability of the foam block 306 to resemble a biasing member, such as a spring. For example, if the foam block 306 is compressed to 25% of its original size, the foam block 306 may exert a force that opposes the applied force over the area of the foam block 306 to which the force is applied. The reactive force may be proportional to the amount the foam block 306 is compressed.

Fluid flow through the foam block 306 may be dependent upon the pore size of the pores within the foam block 306, the stiffness of the foam block 306, and the area of the foam block 306. For example, the foam block 306 may permit a higher flow rate through the foam block 306 if the pores of the foam block 306 are larger than a foam block 306 having smaller pores. Similarly, if the foam block 306 is compressed, a foam block 306 having a higher CFD may permit a higher flow rate than a foam block of comparable size but having a lower CFD. In some embodiments, if the foam block 306 is compressed to 25% of its original size, the foam block 306 may accommodate a fluid flow rate of about 0.5 cubic centimeters per minute.

The fluid enclosure 302 may also include a first sheet 308 and a second sheet 310. The first sheet 308 and the second sheet 310 may be positioned on opposite sides of the foam block 306, and perimeter portions of the first sheet 308 and the second sheet 310 may be coupled to one another to form a chamber 312 having the foam block 306 disposed therein. In some embodiments, the first sheet 308 and the second sheet 310 may be coupled by welding, bonding, or adhering, for example. The first sheet 308 and the second sheet 310 may be an elastomeric film or membrane that can provide a seal adequate to fluidly isolate the foam block 306 from the ambient environment. In some example embodiments, the first sheet 308 and the second sheet 310 may be a polymer drape, such as a polyurethane film, that is permeable to water vapor but impermeable to liquid. Such drapes typically have a thickness in the range of about 25 microns to about 50 microns. In some embodiments, the first sheet 308 and the second sheet 310 may be a single sheet folded on itself to form the chamber 312.

The fluid enclosure 302 may also be coupled to or include the fluid inlet 314 and the fluid outlet 316. The fluid inlet 314 and the fluid outlet 316 may be fluid couplings or ports. In some embodiments, the first sheet 308 and the second sheet 310 may be coupled to the fluid inlet 314 and the fluid outlet 316. Generally, the fluid inlet 314 and the fluid outlet 316 may provide a fluid communication path across the first sheet 308 and the second sheet 310 to permit fluid communication with the chamber 312. The fluid inlet 314 and the fluid outlet 316 can permit the fluid enclosure 302 to be fluidly coupled to both upstream and downstream devices, such as a sealed space formed by the cover 108 and the fluid source 114. Generally, both the fluid inlet 314 and the fluid outlet 316 may permit fluid flow into and out of the chamber 312.

In some embodiments, the fluid outlet 316 may be a calibrated orifice. A calibrated orifice may be a restriction in a fluid system setting a maximum flow rate for the system. In some embodiments, the fluid outlet 316 may be calibrated to allow a maximum flow rate of about 10 cubic centimeters per minute with a 125 mm Hg differential pressure.

The pressure enclosure 304 may enclose, envelope, or otherwise contain the fluid enclosure 302. The pressure enclosure 304 may include a first sheet 318 and a second sheet 320. Furthermore, the first sheet 318 and the second sheet 320 may be positioned on opposite sides of the fluid enclosure 302, and perimeter portions of the first sheet 318 and the second sheet 320 may be coupled to one another to form a chamber 322 having the fluid enclosure 302 disposed therein. In some embodiments, the first sheet 318 and the second sheet 320 may be coupled by welding, bonding, or adhering, for example. The first sheet 318 and the second sheet 320 may be an elastomeric film or membrane that can provide a seal adequate to fluidly isolate the chamber 322 from the ambient environment. In some example embodiments, the first sheet 318 and the second sheet 320 may be a polymer drape, such as a polyurethane film, that is permeable to water vapor but impermeable to liquid. Such drapes typically have a thickness in the range of about 25 microns to about 50 microns. In some embodiments, the first sheet 318 and the second sheet 320 may be a single sheet folded on itself to form the chamber 322. The pressure enclosure 304 may be sealed to the fluid inlet 314 and the fluid outlet 316 so that the chamber 322 may not be in fluid communication with the ambient environment or with the chamber 312 of the fluid enclosure 302 through the fluid inlet 314 or the fluid outlet 316.

The pressure enclosure 304 may also include a pressure outlet 324. The pressure outlet 324 may be a fluid port coupled to the first sheet 318 or the second sheet 320. The pressure outlet 324 may provide a fluid communication path across the first sheet 318 or the second sheet 320, permitting the chamber 322 of the pressure enclosure 304 to be fluidly coupled to other devices, such as the negative-pressure source 104.

The tube 122 may be coupled to the pressure outlet 324 and further fluidly coupled to a negative-pressure source, such as the negative-pressure source 104. The tube 120 may be fluidly coupled to a fluid source, such as the fluid source 114, and to the fluid inlet 314. A second tube 120 may be fluidly coupled to the fluid outlet 316 and then to the connector 118. In some embodiments, the fluid inlet 314 may be directly coupled to the fluid source 114, and the tube 120 may be coupled to the fluid outlet 316 and the connector 118. Fluid may flow from the fluid source 114 through the chamber 312 of the fluid enclosure 302 and to the tissue site. The negative-pressure source 104 may be operated to draw fluid from the sealed space adjacent to the tissue site and through the pressure outlet 324. Fluid removal from the sealed space may generate a negative pressure in the sealed therapeutic environment and a pressure gradient through the tube 120. For example, the pressure at the tube 120 coupled to the connector 118 may be less than the pressure at the tube 120 coupled to the fluid source 114. The pressure gradient through the tube 120 may draw fluid from the fluid source 114 through the irrigation valve 300 and to the sealed therapeutic environment.

Figure 3D:
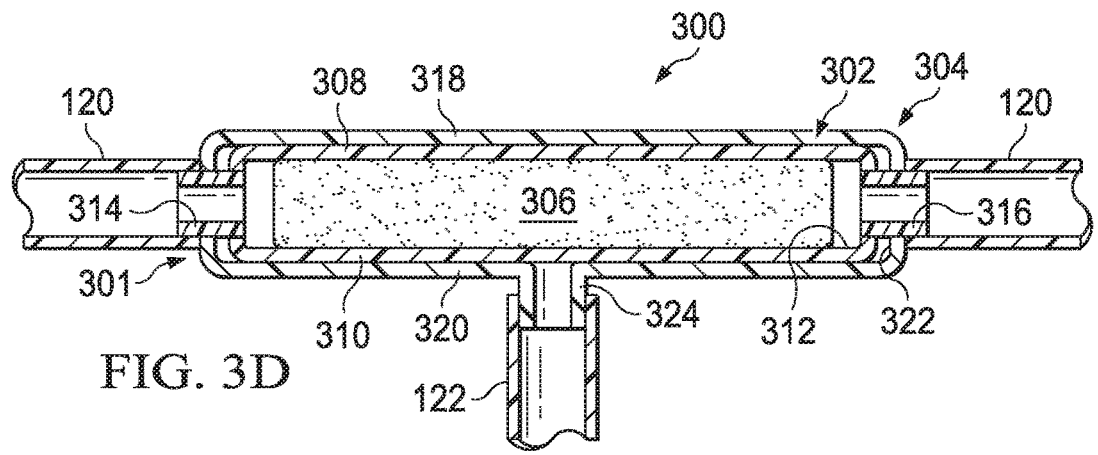
FIG. 3D is a schematic sectional view illustrating additional details of the irrigation valve of FIG. 3A in a low-flow position.

As fluid is drawn from the chamber 322 of the pressure enclosure 304, a differential pressure between the chamber 322 and the ambient environment may collapse the first sheet 318 and the second sheet 320 against the fluid enclosure 302. As more fluid is drawn from the chamber 322, the pressure enclosure 304 may compress the fluid enclosure 302 and the foam block 306, as shown in FIG. 3D. Generally, the CFD of the foam block 306 may be selected to prevent collapse of the foam block 306 until a threshold pressure is developed in the chamber 322 that, if applied over a surface area of the fluid enclosure 302, may generate a compressive force on the fluid enclosure 302. In some embodiments, the threshold pressure may be about 75 mm Hg of negative pressure. Once the threshold pressure is crossed, the force exerted on the fluid enclosure 302 by the pressure enclosure 304 may overcome the CFD of the foam block 306, compressing the foam block 306. In some embodiments, as the negative pressure in the chamber 322 reaches about 125 mm Hg, the foam block 306 may be compressed to about 25% of the original size of the foam block 306. Compression of the foam block 306 may partially block some of the fluid pathways in the foam block 306, restricting fluid flow through the fluid enclosure 302. For example, if a negative pressure of about 125 mm Hg is developed in the chamber 322, the foam block 306 may be compressed so that the fluid pathways of the foam block 306 permit about 0.5 cubic centimeters per minute of fluid flow through the chamber 312.

If the negative-pressure source 104 is turned off, the negative pressure in the chamber 322 and in the sealed space adjacent to the tissue site may gradually decrease. For example, leaks in the cover 108 or inflow of fluid from the body into the sealed therapeutic environment may decrease the negative pressure in the sealed therapeutic environment. As the pressure begins to equalize with the ambient pressure, the foam block 306 may expand, opening the fluid pathways of the foam block 306. Flow may flow through the irrigation valve 300 to the sealed space adjacent to the tissue site at the increased flow rate.

The systems, apparatuses, and methods described herein may provide significant advantages. For example, the irrigation valve 116 my permit the application of an irrigation fluid to a wound from a simple, potentially disposable device, using existing vacuum therapy systems. The irrigation valve may also be used in the home and in emerging markets with little oversight. The irrigation valve may also be used with existing negative-pressure therapy system and devices without requiring a dedicated irrigation therapy pump.

The irrigation valve 116 can also provide controlled irrigation in a compact device. For example, the irrigation valve 116 may be lightweight and sized to provide a known fluid flow for given conditions. A trauma center or emergency vehicle may have multiple irrigation valves sized to provide different flow rates at a same negative-pressure so that irrigation can be provided based on the needs of the tissue site. Furthermore, the irrigation valves may be made from materials that make disposal cost effective. In addition, the irrigation valve 116 can provide irrigation of a tissue site using a volume of fluid that is comparable to instillation therapy devices.

The irrigation valve 116 may also be orientation insensitive. For example, the irrigation valve may operate as intended regardless of the position of the irrigation valve or the orientation of the irrigation valve relative to the force of gravity. In some embodiments, the irrigation valve 116 may be driven by the negative-pressure source 104. For example, the negative-pressure source 104 may drive the jaw 220. In some embodiments, the negative-pressure source 104 may directly drive the jaw 220. In some embodiments, the negative-pressure source 104 may provide negative pressure to the sealed space adjacent the tissue site and the irrigation valve 116.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A system for irrigating a tissue site, comprising:
   a tissue interface configured to be placed adjacent to the tissue site;
   a sealing member configured to be placed over the tissue interface to form a sealed space;
   a negative-pressure source configured to be fluidly coupled to the sealed space;
   a fluid source; and
   an irrigation valve comprising:
      a fluid inlet configured to be fluidly coupled to the fluid source,
      a fluid outlet configured to be fluidly coupled to the sealed space, and
      a clamp actuated by the negative-pressure source to regulate fluid flow from the fluid source through the fluid outlet;
   wherein the clamp comprises:
      a first bar having a first end and a second end,
      a second bar coupled to the second end of the first bar, and
      a piston coupled to the first bar on a same side of the first bar as the second bar, the piston having a chamber configured to be fluidly coupled to the negative-pressure source.

2. The system of claim 1, wherein:
   the piston further comprises:
      a piston head disposed in the chamber, and
      a biasing member disposed in the chamber and operable to bias the piston head to a first position; and
   the clamp further comprises:
      a rod coupled to the piston head; and
      a jaw coupled to the rod and configured to receive a tube, the piston head and the rod operable to move the jaw toward the second bar if negative-pressure in the chamber exceeds a threshold negative pressure.

3. The system of claim 2, wherein the jaw comprises:
   a first leg coupled to the rod; and
   a cross leg coupled to the first leg, the cross leg being substantially perpendicular to the first leg.

4. The system of claim 3, wherein the jaw further comprises a second leg coupled to an end of the cross leg opposite the first leg, the second leg parallel to the first leg and extending toward the second bar.

5. The system of claim 4, wherein the first leg, the second leg, the cross leg, and the second bar form a passageway.

6. The system of claim 2, further comprising a tube having a sidewall, a lumen, and a recess formed in a portion of the sidewall adjacent to the lumen, the recess being semicircular, the tube disposed between the jaw and the second bar, the fluid inlet coupled to a first end of the tube and the fluid outlet coupled to a second end of the tube.

7. The system of claim 6, wherein the recess extends a length of the tube.

8. The system of claim 6, wherein the recess has a length greater than a width of the clamp.

9. The system of claim 6, wherein the lumen is sized to provide a flow of about 10 cubic centimeters per minute.

10. The system of claim 6, wherein the recess is sized to provide a flow of about 0.5 cubic centimeters per minute.

11. The system of claim 1, wherein the negative-pressure source provides negative pressure to the sealed space and the irrigation valve.

12. An irrigation valve, comprising:
a jaw configured to receive a tube;
a first bar having a first end and a second end,
a second bar coupled to the second end of the first bar;
a piston coupled to the jaw and the first bar on a same side of the first bar as the second bar; the piston operable to move the jaw in response to negative pressure; and
wherein the piston comprises:
- a chamber configured to be fluidly coupled to a negative-pressure source,
- a piston head disposed in the chamber, and
- a biasing member disposed in the chamber and operable to bias the piston head to a first position; and wherein the piston is operable to cycle the jaw between a high-flow position and a low-flow position to control fluid flow through the tube.

13. The irrigation valve of claim 12, wherein the tube comprises a sidewall, a lumen, and a recess formed in a portion of the sidewall adjacent to the lumen.

14. The irrigation valve of claim 13, wherein the recess extends a length of the tube.

15. The irrigation valve of claim 13, wherein the recess has a length greater than a width of the jaw.

16. The irrigation valve of claim 12, wherein the tube is sized to provide a flow of about 10 cubic centimeters per minute and a differential pressure of about 75 mm Hg or less across the tube.

17. The irrigation valve of claim 12, wherein the tube is sized to provide a flow of about 0.5 cubic centimeters per minute and a differential pressure of about 125 mm Hg or less across the tube.

18. The irrigation valve of claim 12, wherein the tube is configured to be fluidly coupled to a fluid source and a sealed space.

19. The irrigation valve of claim 12, further comprising:
a rod having a first end coupled to the piston head and a second end coupled to the jaw; and
the piston head being operable to move the jaw toward the base if a negative pressure in the chamber exceeds a threshold.

20. The irrigation valve of claim 19, wherein the first bar and the second bar are coupled to each other to form an angle $\alpha$.

21. The irrigation valve of claim 20, wherein the jaw comprises:
a first leg coupled to the rod; and
a cross leg coupled to the first leg, the cross leg being substantially perpendicular to the first leg.

22. The irrigation valve of claim 21, wherein the jaw further comprises a second leg coupled to an end of the cross leg opposite the first leg, the second leg parallel to the first leg and extending toward the base.

23. The irrigation valve of claim 22, wherein the first leg, the second leg, the cross leg, and the second bar form a passageway.

24. The irrigation valve of claim 12, wherein a negative-pressure source drives the jaw.

25. The irrigation valve of claim 12, wherein a negative-pressure source directly drives the jaw.

26. A method for irrigating a tissue site, the method comprising:
placing a tissue interface adjacent to the tissue site;
covering the tissue interface and the tissue site to form a sealed space;
fluidly coupling an irrigation valve to the sealed space, the irrigation valve comprising:
a first bar having a first end and a second end,
a second bar coupled to the second end of the first bar, and
a piston coupled to the first bar on a same side of the first bar as the second bar, the piston having a chamber;
fluidly coupling a fluid source to the irrigation valve;
fluidly coupling a negative-pressure source to the sealed space and the chamber of the irrigation valve;
operating the negative-pressure source to supply negative-pressure to the sealed space and the irrigation valve; and
restricting a fluid path through the irrigation valve in response to a supply of negative pressure.

27. The method of claim 26, further comprising:
supplying negative pressure at about 75 mm Hg; and
drawing fluid through the fluid path at about 10 cubic centimeters per minute.

28. The method of claim 26, further comprising:
supplying negative pressure at about 125 mm Hg; and
drawing fluid through the fluid path at about 0.5 cubic centimeters per minute.

29. The method of claim 26, wherein restricting a fluid path comprises operating a clamp to compress a tube fluidly coupled between the fluid source and the sealed space.

* * * * *